(12) United States Patent
Daniel et al.

(10) Patent No.: US 9,687,588 B2
(45) Date of Patent: Jun. 27, 2017

(54) PLACENTAL TISSUE GRAFTS PRODUCED BY CHEMICAL DEHYDRATION/FREEZE-DRYING AND METHODS FOR MAKING AND USING THE SAME

(71) Applicant: MiMedx Group, Inc., Marietta, GA (US)

(72) Inventors: John Daniel, Marietta, GA (US); Randall Spencer, Marietta, GA (US); Steven Ray, Marietta, GA (US)

(73) Assignee: MiMedx Group, Inc., Marietta, GA (US)

( * ) Notice: Subject to any disclaimer, the term of this patent is extended or adjusted under 35 U.S.C. 154(b) by 24 days.

(21) Appl. No.: 14/932,874

(22) Filed: Nov. 4, 2015

(65) Prior Publication Data

US 2016/0051730 A1 Feb. 25, 2016

Related U.S. Application Data

(62) Division of application No. 13/691,508, filed on Nov. 30, 2012, now Pat. No. 9,186,382.

(60) Provisional application No. 61/566,057, filed on Dec. 2, 2011.

(51) Int. Cl.
*A61K 35/50* (2015.01)
*A61L 27/36* (2006.01)

(52) U.S. Cl.
CPC .......... *A61L 27/3687* (2013.01); *A61K 35/50* (2013.01); *A61L 27/3604* (2013.01); *A61L 27/3691* (2013.01); *A61L 2430/02* (2013.01); *A61L 2430/38* (2013.01)

(58) Field of Classification Search
None
See application file for complete search history.

(56) References Cited

U.S. PATENT DOCUMENTS

| | | |
|---|---|---|
| 8,372,438 B2 | 2/2013 | Daniel et al. |
| 2004/0048796 A1 | 3/2004 | Hariri et al. |
| 2008/0069895 A1 | 3/2008 | Liu et al. |
| 2009/0258082 A1 | 10/2009 | Nikaido et al. |
| 2010/0104539 A1 | 4/2010 | Daniel et al. |

FOREIGN PATENT DOCUMENTS

| | | |
|---|---|---|
| WO | WO-2009/033160 A1 | 3/2009 |
| WO | WO-2012/112410 A2 | 8/2012 |
| WO | WO-2012/112441 A1 | 8/2012 |

OTHER PUBLICATIONS

Gajiwala et al., "Evaluation of lyophilised, gamma-irradiated amnion as a biological dressing," Cell Tissue Bank., (2004), 5(2):73-80.
PCT International Search Report and Written Opinion in related PCT Application No. PCT/US12/67270, dated Feb. 28, 2013.
PCT International Preliminary Report on Patentability in related PCT Application No. PCT/US12/67270 dated Dec. 20, 2013.
Rodriguez-Ares et al, Acta Ophthalmological, 2009, vol. 87, pp. 396-403.
Ward et al, British Journal of Plastic Surgery, 1989, vol. 42, pp. 463-467.

*Primary Examiner* — Allison Fox
(74) *Attorney, Agent, or Firm* — Alston & Bird LLP

(57) ABSTRACT

Described herein are placental tissue grafts produced by chemical dehydration followed by freeze-drying the placental tissue to produce the tissue graft. The tissue grafts retain their biological properties preferably at the same level as the placental tissues before they are processed. The placental tissue grafts have numerous medical applications. Methods for making the tissue graft compositions are also described herein.

13 Claims, 1 Drawing Sheet

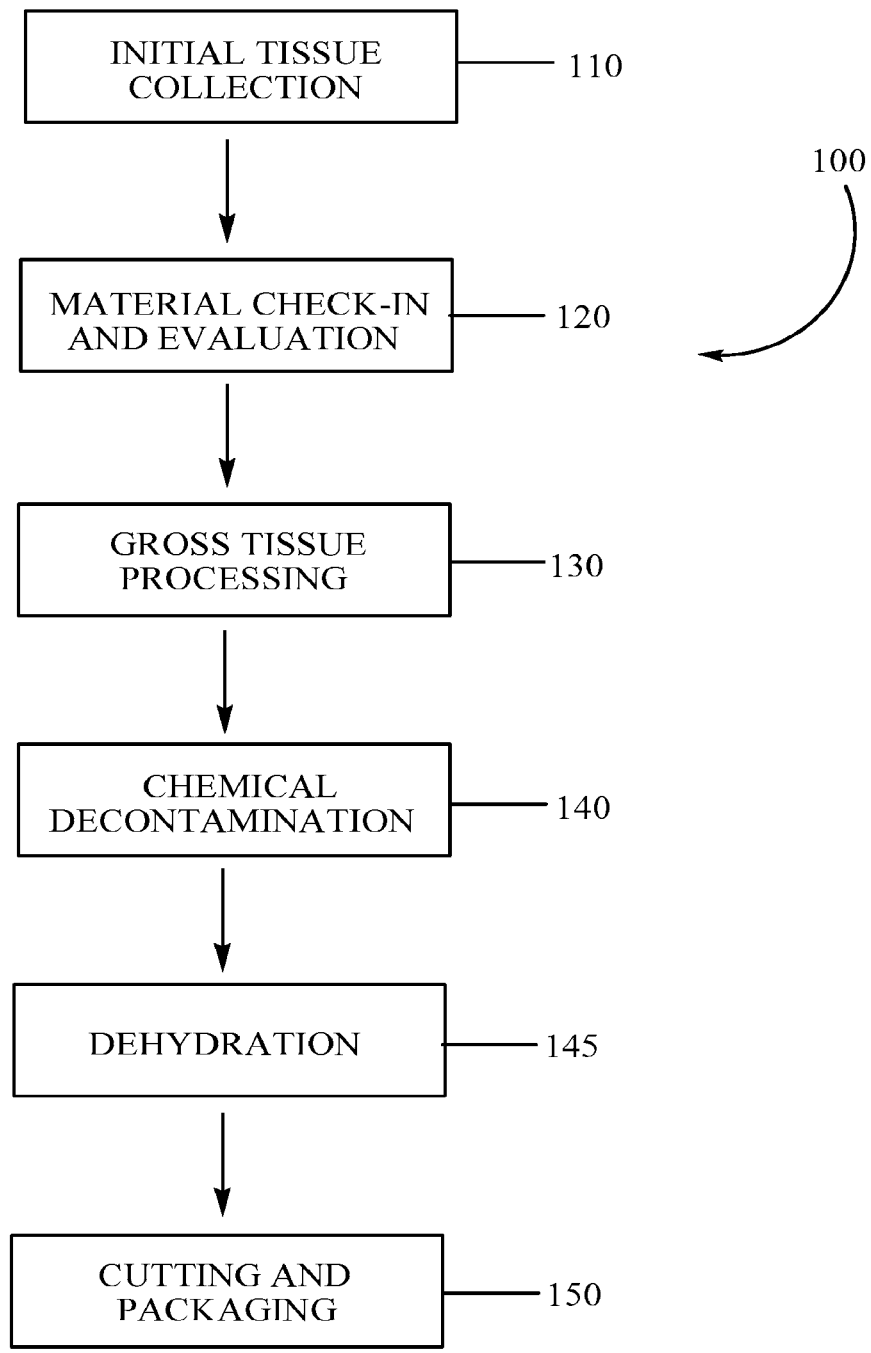

PLACENTAL TISSUE GRAFTS PRODUCED BY CHEMICAL DEHYDRATION/FREEZE-DRYING AND METHODS FOR MAKING AND USING THE SAME

CROSS-REFERENCE TO RELATED APPLICATION

This application is a divisional of U.S. patent application Ser. No. 13/691,508, filed Nov. 30, 2012, which claims the benefit of U.S. Provisional Application No. 61/566,057, filed Dec. 2, 2011, each of which are incorporated herein by reference in their entirety.

FIELD OF THE INVENTION

This invention relates to placental tissue grafts, methods of preparing the tissue grafts, compositions and uses thereof.

SUMMARY OF THE INVENTION

Described herein are placental tissue grafts produced by chemical dehydration followed by freeze-drying the placental tissue to produce the tissue graft. The tissue grafts preferably are undamaged during the dehydration process and retain biological properties preferably at the same level as the placental tissues before they are processed. The placental tissue grafts have numerous medical applications. Methods for making the tissue graft compositions are also described herein.

The advantages of the invention will be set forth in part in the description which follows, and in part will be apparent from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIG. 1 is an overview flow chart of the process for making the tissue graft compositions described herein.

DETAILED DESCRIPTION

Before the present articles and methods are disclosed and described, it is to be understood that the aspects described below are not limited to specific articles, compositions, preparations and/or methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "subject" as used herein is any vertebrate organism, including mammals. In one embodiment, the subject is a human.

The term "placenta" or "harvested placenta" as used herein refers to the placenta obtained from a female mammal during or after a child birth as is well known in the art.

The term "placental tissue" refers to one or more of the individual components of the placenta (but not the entire placenta). Such components are well known in the art and include, amnion, chorion, Wharton's jelly and any combination thereof. Included within the term "amnion" are unmodified and modified amnion. Modified amnion includes amnion in which the epithelial layer has been removed (mechanically, chemically or enzymatically) while retaining the fibroblast cellular layer, amnion which has been completely decellularized as well as amnion which retains the epithelial layer while having the fibroblast layer removed.

The term "placental tissue graft" refers to one or more layers of placental tissue which have been processed as per this invention and are suitable for use as a graft in treating a condition in a mammal such as a human.

Titles or subtitles may be used in the specification for the convenience of a reader, which are not intended to influence the scope of the present invention. Additionally, some terms used in this specification are more specifically defined below.

I. Tissue Grafts and Methods for Making Thereof

Described herein are tissue grafts and methods of making and using thereof. In one aspect, the tissue grafts are produced by a process comprising:

a. chemically dehydrating a harvested placental tissue; and b. freeze-drying the placental tissue to produce the tissue graft.

In some embodiments, the placental tissue graft comprises at least two layers of chorion, at least two layers of amnion membrane, or at least one layer of chorion and at least one layer of amnion membrane.

In some embodiments, the placental tissue graft comprises amnion membrane/Wharton's jelly/chorion. In some embodiments, the placental tissue graft comprises at least one layer of chorion and at least one layer of amnion membrane, and further comprises Wharton's jelly intermediate between the amnion membrane and chorion membrane.

In another aspect, provided is a method for producing a placental tissue graft, which method comprises:

a. chemically dehydrating a placental tissue; and b. freeze-drying the placental tissue to produce the tissue graft.

In some embodiments, the method further comprises, prior to step (a), laminating two or more layers selected from amnion, Wharton's jelly and/or chorion membranes prior to dehydration. In some embodiments, two or more layers of amnion membranes are laminated. In some embodiments, two or more layers of chorion membranes are laminated. In some embodiments, at least one layer of amnion membrane and at least one layer of chorion membrane are laminated. In some embodiments, at least one layer of amnion membrane, at least one layer of Wharton's jelly and at least one layer of chorion membrane are laminated.

In some embodiments, the method further comprises, prior to step (a), chemically decontaminating the placental tissue. In some embodiments, the decontaminating step is prior to the laminating step. In some embodiments, the placental tissue is decontaminated by being soaked in an antibiotic solution and/or a detergent.

In some embodiments, the method further comprises physically cleaning the placental tissue to remove blood clots and other contaminates.

In some embodiments, step (a) comprises contacting the placental tissue with a sufficiently amount of a polar organic solvent for a sufficient time in order to substantially or completely remove residual water present in the placental tissue. In some embodiments, step (a) comprises soaking the placental tissue in a polar organic solvent at room temperature. In some embodiments, the polar organic solvent comprises an alcohol, a ketone, an ether, an aldehyde, or any combination thereof. In some embodiments, the polar organic solvent comprises DMSO, acetone, tetrahydrofuran, ethanol, isopropanol, or any combination thereof.

In some embodiments, the placental tissue is freeze-dried at a temperature of from −50° C. to −80° C.

In some embodiments, step (b) comprises (1) laying one or more chemically dehydrated placental tissue on a substrate and (2) inserting the substrate with the one or more placental tissue in a freeze-dryer. In some embodiments, the substrate is a bowl, pan, screen, frame, or drying fixture.

The method and additional steps that can be included in the method are exemplified in detail below.

FIG. 1 depicts an exemplary, non-limiting overview (100) and certain aspects of the steps to harvest, process, and prepare placental tissues for use in the preparation of the tissue grafts described herein. More detailed descriptions and discussion regarding each individual step will follow. Initially, the placenta is collected (step 110). The material is preserved and transported in conventional tissue preservation manner to a suitable processing location or facility for check-in and evaluation (step 120). Gross processing, handling, and separation of the placental or placental tissue then takes place (step 130). Acceptable placenta or placental tissue is then decontaminated (step 140). After decontamination, the placental tissue is chemically dehydrated and freeze-dried (step 145). Each step is described in detail below.

Initial Tissue Collection (Step 110)

The components used to produce the tissue grafts are derived from the placenta. The source of the placenta can vary. In one aspect, the placenta is derived from a mammal such as human and other animals including, but not limited to, cows, pigs, and the like. In the case of humans, the recovery of the placenta originates in a hospital, where it is collected during a Cesarean section birth. The donor, referring to the mother who is about to give birth, voluntarily submits to a comprehensive screening process designed to provide the safest tissue possible for transplantation. The screening process preferably tests for antibodies to the human immunodeficiency virus type 1 and type 2 (anti-HIV-1 and anti-HIV-2), antibodies to the hepatitis B virus (anti-HBV) hepatitis B surface antigens (HBsAg), antibodies to the hepatitis C virus (anti-HCV), antibodies to the human T-lymphotrophic virus type I and type II (anti-HTLV-I, anti-HTLV-II), CMV, and syphilis, and nucleic acid testing for human immune-deficiency virus type 1 (HIV-1) and for the hepatitis C virus (HCV), using conventional serological tests. The above list of tests is exemplary only, as more, fewer, or different tests may be desired or necessary over time or based upon the intended use of the grafts, as will be appreciated by those skilled in the art.

Based upon a review of the donor's information and screening test results, the donor will either be deemed acceptable or not. In addition, at the time of delivery, cultures are taken to determine the presence of bacteria, for example, *Clostridium* or *Streptococcus*. If the donor's information, screening tests, and the delivery cultures are all satisfactory (i.e., do not indicate any risks or indicate acceptable level of risk), the donor is approved by a medical director and the tissue specimen is designated as initially eligible for further processing and evaluation.

Human placentas that meet the above selection criteria are preferably bagged in a saline solution in a sterile shipment bag and stored at a low temperature (e.g., −1° C.-10° C., 0° C.-10° C., 1° C.-10° C., or 0° C.-5° C.), such as in a container of wet ice, for shipment to a processing location or laboratory for further processing.

If the placenta is collected prior to the completion or obtaining of results from the screening tests and delivery cultures, such placenta or placental tissue is labeled and kept in quarantine. The placenta is approved for further processing only after the required screening assessments and delivery cultures, which declare the placenta or placental tissue safe for handling and use, are satisfied and obtain final approval from a medical director.

Material Check-in and Evaluation (Step 120)

Upon arrival at the processing center or laboratory, the shipment is opened and verified that the sterile shipment bag/container is still sealed and in the coolant, that the appropriate donor paperwork is present, and that the donor number on the paperwork matches the number on the sterile shipment bag containing the placenta or placenta tissue. The sterile shipment bag containing the tissue is then stored at a low temperature (e.g., −1° C.-10° C., 0° C.-10° C., 1° C.-10° C., or 0° C.-5° C.), such as in a refrigerator until ready for further processing.

Gross Tissue Processing (Step 130)

When the placenta or placental tissue is ready to be processed further, the sterile supplies necessary for processing the placenta or placental tissue further are assembled in a staging area in a controlled environment and are prepared for introduction into a controlled environment. In one aspect, the placenta is processed at room temperature. If the controlled environment is a manufacturing hood, the sterile supplies are opened and placed into the hood using conventional sterilization techniques. If the controlled environment is a clean room, the sterile supplies are opened and placed on a cart covered by a sterile drape. The work surfaces are covered by sterile drape using conventional sterilization techniques, and the sterile supplies and the processing equipment are placed onto the sterile drape, again using conventional sterilization techniques.

Processing equipment is decontaminated according to conventional and industry-approved decontamination procedures and then introduced into the controlled environment. The equipment is strategically placed within the controlled environment to minimize the chance for the equipment to come in proximity to or is inadvertently contaminated by the tissue specimen.

Next, the placenta is removed from the sterile shipment bag and transferred aseptically to a sterile processing basin within the controlled environment. The sterile basin contains hyperisotonic saline solution (e.g., 18% NaCl) that is at room or near room temperature. The placenta is gently massaged to help separate blood clots and to allow the placental tissue to reach room temperature, which facilitates the separation of the placental components from each other (e.g., amnion membrane and chorion). After having warmed up to the ambient temperature (e.g., after about 10-30 minutes), the placenta is then removed from the sterile processing basin and laid flat on a processing tray with the amnion membrane layer facing down for inspection.

The placenta is examined for discoloration, debris or other contamination, odor, and signs of damage. The size of the placenta or placental tissue is also noted. A determination is made, at this point, as to whether the placenta or placental tissue is acceptable for further processing. In one embodiment, the placenta is acceptable for further processing if no discoloration, debris, unacceptable odor, and/or signs of damage is observed.

In one aspect, if the placenta is deemed acceptable for further processing, the amnion membrane, Wharton's jelly, and chorion are collectively dissected from the placenta. In this aspect, the amnion membrane, Wharton's jelly, and chorion are not separated from one, and this resulting placental tissue is further processed as discussed below.

In another aspect, the amnion membrane and chorion of the placenta can be carefully separated. In one aspect, the materials and equipment used in this procedure include a processing tray, 18% saline solution, sterile 4×4 sponges, and two sterile Nalgene jars. The placenta is then closely examined to find an area (typically a corner) in which the amnion membrane can be separated from the chorion. The amnion membrane appears as a thin, opaque layer on the chorion.

The fibroblast layer is identified by gently contacting each side of the amnion membrane with a piece of sterile gauze or a cotton tipped applicator. The fibroblast layer will stick to the test material. The amnion membrane is placed into processing tray basement membrane layer down. Using a blunt instrument, a cell scraper or sterile gauze, any residual blood is also removed. This step is done with adequate care, again, so as not to tear the amnion membrane. The cleaning of the amnion membrane is complete once the amnion membrane is smooth and opaque-white in appearance.

In certain aspects, the intermediate tissue layer is removed from the amnion membrane. This can be performed by peeling the intermediate tissue layer from the amnion membrane. Alternatively, the intermediate tissue layer can be removed from the amnion membrane by wiping the intermediate tissue layer with a gauze or other suitable wipe. The resulting amnion can be subsequently decontaminated using the process described below. The intermediate tissue layer does not require any additional processing and can be used as-is.

In certain aspects, the Wharton's jelly can optionally be isolated using the following procedure. Using a scalpel or scissors, the umbilical cord is dissected away from the chorionic disk. Once the veins and the artery have been identified, the cord is dissected lengthwise down one of the veins or the artery. Once the umbilical cord has been dissected, surgical scissors and forceps can be used to dissect the vein and artery walls from the Wharton's jelly. Next, the outer layer of amnion membrane is removed from the Wharton's jelly by cutting the amnion membrane. After removing the amnion membrane from the Wharton's jelly, the Wharton's jelly can be cut into strips. In one aspect, the strips are approximately 1-4 cm by 10-30 cm with an approximate thickness of 1.25 cm; however, other sizes and/or thicknesses are possible depending on application.

Chemical Decontamination (Step 140)

Any of the placenta or placental tissues discussed herein can be chemically decontaminated using the techniques described below. In one aspect, the placenta or placental tissue is decontaminated at room temperature. In one aspect, the amnion membrane produced in step 130 can be placed into a sterile Nalgene jar for the next step. In one aspect, the following procedure can be used to clean the amnion membrane. Each Nalgene jar is aseptically filled with 18% saline hypertonic solution and sealed (or sealed with a top). The jar is then placed on a rocker platform and agitated for between 30 and 90 minutes, which further cleans the amnion membrane of contaminants. If the rocker platform is not in the critical environment (e.g., the manufacturing hood), the Nalgene jar is returned to the controlled/sterile environment and opened. Using sterile forceps or by aseptically decanting the contents, the amnion membrane is gently removed from the Nalgene jar containing the 18% hyperisotonic saline solution and placed into an empty Nalgene jar. This empty Nalgene jar with the amnion membrane is then aseptically filled with a pre-mixed antibiotic solution. In one aspect, the premixed antibiotic solution is composed of a cocktail of antibiotics, such as Streptomycin Sulfate and Gentamicin Sulfate. Other antibiotics, such as Polymixin B Sulfate and Bacitracin, or similar antibiotics now available or available in the future, are also suitable. Additionally, it is preferred that the antibiotic solution be at room temperature when added so that it does not change the temperature of or otherwise damage the amnion membrane. This jar or container containing the amnion membrane and antibiotics is then sealed or closed and placed on a rocker platform and agitated for, preferably, between 60 and 90 minutes. Such rocking or agitation of the amnion membrane within the antibiotic solution further cleans the tissue of contaminants and bacteria. Optionally, the amnion membrane can be washed with a detergent. In one aspect, the amnion membrane can be washed with 0.1 to 10%, 0.1 to 5%, 0.1 to 1%, or 0.5% Triton-X wash solution.

If the rocker platform is not in the critical environment (e.g., the manufacturing hood), the jar or container containing the amnion membrane and antibiotics is then returned to the critical/sterile environment and opened. Using sterile forceps, the amnion membrane is gently removed from the jar or container and placed in a sterile basin containing sterile water or normal saline (0.9% saline solution). The amnion membrane is allowed to soak in place in the sterile water/normal saline solution for at least 10 to 15 minutes. The amnion membrane may be slightly agitated to facilitate removal of the antibiotic solution and any other contaminants from the tissue. After at least 10 to 15 minutes, the amnion membrane is ready to be dehydrated and processed further.

In the case when the chorion is to be used, the following exemplary procedure can be used. After separation of the chorion from the amnion membrane and removal of clotted blood from the fibrous layer, the chorion is rinsed in 18% saline solution for 15 minutes to 60 minutes. During the first rinse cycle, 18% saline is heated in a sterile container using a laboratory heating plate such that the solution temperature is approximately 48° C. The solution is decanted, the chorion tissue is placed into the sterile container, and decanted saline solution is poured into the container. The container is sealed and placed on a rocker plate and agitated for 15 minutes to 60 minutes. After 1 hour agitation bath, the chorion tissue was removed and placed into second heated agitation bath for an additional 15 minutes to 60 minutes rinse cycle. Optionally, the chorion tissue can be washed with a detergent (e.g., Triton-X wash solution) as discussed above for the amnion membrane. The container is sealed and agitated without heat for 15 minutes to 120 minutes. The chorion tissue is next washed with deionized water (250 milliliter (mL) of DI water×4) with vigorous motion for each rinse. The tissue is removed and placed into a container of 1×PBS w/EDTA solution. The container is sealed and agitated for 1-8 hours at controlled temperature. The chorion tissue is removed and rinsed using sterile water. A visual inspection was performed to remove any remaining discolored fibrous blood material from the chorion tissue. The chorion tissue should have a cream white visual appearance with no evidence of brownish discoloration.

In the case of the decontamination of Wharton's jelly, it can be transferred to a sterile Nalgene jar. Next, room temperature 18% hypertonic saline solution is added to rinse the tissue and the jar is sealed. The jar is agitated for 30 to 60 minutes. After incubation, the jar is decontaminated and returned to the sterile field. The tissue is transferred to a clean sterile Nalgene jar and prewarmed (about 48° C.) 18% NaCl is added. The container is sealed and placed on a rocker plate and agitated for 60 to 90 minutes.

In one aspect, after the rinse, the jar is decontaminated and returned to the sterile field. The tissue is removed and placed into an antibiotic solution. The container is sealed and agitated for 60 to 90 minutes on a rocker platform. Following incubation, the jar may be refrigerated at 1 to 10° C. for up to 24 hours. The Wharton's jelly is next transferred to a sterile basin containing approximately 200 mL of sterile water. The tissue is rinsed for 1-2 minutes and transferred to a sterile Nalgene jar containing approximately 300 mL of sterile water. The jar is sealed and placed on the rocker for 30 to 60 minutes. After the incubation, the jar is returned to the sterile field. The Wharton's jelly should have a cream white visual appearance with no evidence of brownish discoloration. The tissue is ready for further processing.

In other aspects, when the placental tissue is amnion membrane, Wharton's jelly, and chorion that has not been separated, the placental tissue can be decontaminated using any of the techniques and solutions described above (e.g., antibiotic solutions, detergents such as Triton X, etc.).

In certain aspects, it is desirable to remove epithelium layer present on the amnion membrane after chemical decontamination. In one aspect, the epithelium layer present on the amnion membrane is substantially removed in order to expose the basement layer of the amnion membrane. The term "substantially removed" with respect to the amount of epithelium removed is defined herein as removing greater than 50%, greater than 60%, greater than 70%, greater than 80%, greater than 90%, greater than 95%, or greater than 99% of the epithelial cells from the amnion. The presence or absence of epithelial cells remaining on the amnion membrane can be evaluated using techniques known in the art. For example, after removal of the epithelial cell layer, a representative tissue sample from the processing lot is placed onto a standard microscope examination slide. The tissue sample is then stained using Eosin Y Stain and evaluated. The sample is then covered and allowed to stand. Once an adequate amount of time has passed to allow for staining, visual observation is done under magnification.

The epithelium layer can be removed by techniques known in the art. For example, the epithelium layer can be scraped off of the amnion using a cell scraper. Other techniques include, but are not limited to, freezing the membrane, physical removal using a cell scraper, or exposing the epithelial cells to nonionic detergents, anionic detergents, and nucleases. The de-epithelialized tissue is then evaluated to determine that the basement membrane has not been compromised and remains intact. This step is performed after completion of the processing step and the tissue has been dehydrated as described in the next section. For example, a representative sample graft is removed for microscopic analysis. The tissue sample is place onto a standard slide and 100 microliter (μL) of Eosin Y stain is applied to the sample and allowed to set. The tissue sample is then examined under magnification. Cellular material will stain dark indicating the presence of cells. If no stained cells are present, de-epithelization has been achieved.

Dehydration (Step 145)

One or more placental tissues prepared above can be dehydrated to produce dehydrated placental tissue grafts. In the case when two or more placental tissues are used, the tissue is a laminate. In one aspect, two or more membranes are laminated prior to dehydration. For example, a laminate composed of amnion, amnion membrane, chorion, Wharton's jelly, or any combination thereof can be produced. In one aspect, the tissue is an amnion/chorion laminate. In another aspect, the tissue has at least two layers of chorion, at least two layers of amnion, or at least one layer of chorion and at least one layer of amnion. In a further aspect, the placental tissue has a plurality chorion and/or amnion membranes laminated to one another.

Techniques for producing laminated tissue are know in the art. For example, a layer of amnion optionally with substantially no epithelial cells on the surface of the basement membrane can be applied to a fixture, one or more amnion and/or chorion membranes can applied to the base amnion layer to form the laminated tissue graft. In some embodiment, a layer of Wharton's jelly can be applied between two layers of amnion membranes, between two layers of chorion membranes, or between one layer of amnion membrane and one layer of chorion membrane.

In one aspect, the tissue is dehydrated by chemical dehydration followed by freeze-drying. In one aspect, the chemical dehydration step is performed by contacting the placental tissue with a polar organic solvent for a sufficient time and amount in order to substantially (i.e., greater than 90%, greater than 95%, or greater than 99%) or completely remove residual water present in the placental tissue (i.e., dehydrate the tissue). The solvent can be protic or aprotic. Examples of polar organic solvents useful herein include, but are not limited to, alcohols, ketones, ethers, aldehydes, or any combination thereof. Specific, non-limiting examples include DMSO, acetone, tetrahydrofuran, ethanol, isopropanol, or any combination thereof. In one aspect, the placental tissue is contacted with a polar organic solvent at room temperature. No additional steps are required, and the placental tissue can be freeze-dried directly as discussed below. In one aspect, the condition for chemical dehydration does not induce cell lysis.

After chemical dehydration, the placental tissue is freeze-dried in order to remove any residual water and polar organic solvent. After drying, the placental tissue graft is prepared.

In one aspect, the placental tissue is placed in a freeze-dryer, and the placental tissue is lyophilized at between −50° C. to −80° C. In another aspect, the placental tissue is placed in a freeze-dryer such that it is hanging in the freeze-dryer. In other aspects, the placental tissue is placed on a substrate that can facilitate free-drying. Examples of such substrates include, but are not limited to, a pan, bowl, screen, or a frame. In one aspect, one or more placental tissues can optionally be laid on a suitable drying fixture prior to freeze-drying. For example, at least two layers of hydrated chorion, at least two layers of hydrated amnion, or at least one layer of hydrated chorion and hydrated amnion can be applied to the drying fixture. In other aspects, the placental tissue composed of amnion membrane, Wharton's jelly, and chorion that has not been separated can be laid on top of the drying fixture, where one or more additional placental tissues such as amnion membrane and/or chorion can optionally be applied on top of the tissue.

The drying fixture is preferably sized to be large enough to receive the placental tissue, fully, in laid out, flat fashion. In one aspect, the drying fixture is made of Teflon or of Delrin, which is the brand name for an acetal resin engineering plastic invented and sold by DuPont and which is also available commercially from Werner Machine, Inc. in Marietta, Ga. Any other suitable material that is heat and cut resistant, capable of being formed into an appropriate shape to receive wet tissue can also be used for the drying fixture.

In one aspect, the receiving surface of the drying fixture can have grooves that define the product spaces, which are the desired outer contours of the tissue after it is cut and of a size and shape that is desired for the applicable surgical procedure in which the tissue graft will be used. For example, the drying fixture can be laid out so that the grooves are in a grid arrangement. The grids on a single drying fixture may be the same uniform size or may include multiple sizes that are designed for different surgical applications. Nevertheless, any size and shape arrangement can be used for the drying fixture, as will be appreciated by those skilled in the art. In another aspect, instead of having grooves to define the product spaces, the drying fixture has raised ridges or blades.

In certain aspects, the drying fixture can include a slightly raised or indented texture in the form of text, logo, name, or similar design. This textured text, logo, name, or design can be customized or private labeled depending upon the company that will be selling the graft or depending upon the desired attributes requested by the end user (e.g., surgeon). When dried, the prepared tissue graft will mold itself around the raised texture or into the indented texture, essentially providing a label within the tissue graft itself. Preferably, the texture/label can be read or viewed on the placental tissue graft in only one orientation so that, after dehydration, an end user (e.g., a surgeon) of the dried tissue graft will be able to identify the top and bottom of the placental tissue. In other aspects, a stamp can be imprinted on the placental tissue graft after freeze-drying in order to differentiate the sides of the graft.

Once the placental tissue(s) is placed on the drying fixture, the drying fixture is placed in the freeze-dryer. The use of the freeze-dryer to dehydrate the placental tissue can be more efficient and thorough compared to other techniques such as thermal dehydration. In general, it is desirable to avoid ice crystal formation in the placental tissue as this may damage the extracellular matrix in the tissue graft. By chemically dehydrating the placental tissue prior to freeze-drying, this problem can be avoided. The chemical-dehydration and freeze-drying method also minimize formation of porous structures within the tissue graft that more likely result from conventional dehydration methods, such as direct lyophilization, and may compromise structure strength of the tissue graft.

The chemical-dehydration and freeze-drying method can prepare ultra dry tissue graft when needed. In one aspect, the ultra-dry material can absorb water or an aqueous solution, such as a solution comprising a biological material useful for promote wound healing, more readily when needed.

In another aspect, the chemical-dehydration and freeze-drying method is capable of forming a physical barrier to prevent adhesion during wound healing as compared with conventional dehydration methods, such as direct lyophilization.

Cutting & Packaging (Step 150)

Once the tissue graft has been adequately dehydrated, the tissue graft is then ready to be cut into specific product sizes and appropriately packages for storage, terminal sterilization, and later surgical use. The number of grafts to be produced is estimated based on the size and shape of the tissue on the drying fixture(s). An appropriate number of pouches, one for each tissue graft, are then also introduced into the sterile/controlled environment.

If the drying fixture has grooves, then the following exemplary procedure is followed for cutting the tissue graft into product sizes. If the drying fixture is configured in a grid pattern, a #20 or similar straight or rolling blade is used to cut along each groove line in parallel. Then, all lines in the perpendicular direction are cut. Alternatively, if the drying fixture has raised edges or blades, then the following procedure is followed for cutting the tissue graft into product sizes. A sterile roller is used to roll across the drying fixture. Sufficient pressure must be applied so that the dehydrated tissue graft is cut along all of the raised blades or edges of the drying fixture.

After cutting, each tissue graft is placed in a respective "inner" pouch. The inner pouch, which preferably has a clear side and an opaque side, should be oriented clear side facing up. The tissue graft is placed in the "inner" pouch so that the texture in the form of text, logo, name, or similar design is facing out through the clear side of the inner pouch and is visible outside of the inner pouch. This process is repeated for each separate graft.

Each tissue graft is then given a final inspection to confirm that there are no tears or holes, that the product size (as cut) is within approximately 1 millimeter (plus or minus) of the specified size for that particular graft, that there are no noticeable blemishes or discoloration of the tissue, and that the textured logo or wording is readable and viewable through the "inner" pouch. The final tissue grafts can be stored at room temperature for extended periods of time.

II. Applications of Tissue Grafts

In one aspect, provided is a wound dressing comprising the tissue graft described herein.

In another aspect, provided is a method for enhancing wound healing in a subject comprising applying the tissue graft described herein to the wound.

In another aspect, provided is a method for preventing or reducing scar formation on or near the spine of a subject after a surgical procedure, the method comprising applying to the subject a tissue graft described herein directly to the spinal dura of the subject or a region near the spine. In some embodiments, the surgical procedure comprises a posterior procedure. In some embodiments, the posterior procedure is a laminectomy or discectomy. In some embodiments, the posterior procedure is an Anterior Lumbar Interbody Fusion (ALIF) and Transforaminal Interbody Fusion (TLIF). In some embodiments, the surgical procedure comprises an anterior procedure. In some embodiments, the method comprises applying the tissue graft directly to the dural tear.

In another aspect, provided is a use of the tissue graft described herein in cranial dura repair, a perioplastic procedure, in the elimination of a frenum pull, the regeneration of lost patella tissue, the repair of the Schneiderian membrane in the sinus cavity, soft tissue around dental implants, vestibuloplasty, and guided tissue regeneration.

In some embodiments, the use is in a dental application. In some embodiments, the use is in an orthopedic application. In some embodiments, the use is in an ENT application. In some embodiments, the use is in an opthalmological application (e.g., on-lay grafts ocular surface repair). In some embodiments, the use is in a gynecological application. In some embodiments, the use is in an urological application. In some embodiments, the use is in a general surgery. In some embodiments, the use is in a cardiac application. In some embodiments, the use is to reduce or prevent scar formation after plastic surgery.

The grafts described herein can be used in numerous medical applications involving wound healing in a subject. In one aspect, the grafts described herein are useful in enhancing or improving wound healing. The types of wounds that present themselves to physicians on a daily bases are diverse. Acute wounds are caused by surgical intervention, trauma and burns. Chronic wounds are wounds that are delayed in closing compared to healing in an otherwise healthy individual. Examples of chronic wound types plaguing patients include diabetic foot ulcers, venous leg ulcers, pressure ulcers, arterial ulcers, and surgical wounds that become infected.

The physician's goal when treating traumatic wounds is to heal the wound while allowing the patient to retain natural function in the area of the wound with minimal scaring and infection. If a wound becomes infected, it can lead to a loss of limb or life. For the most part, physicians heal these patients without incident. However, physicians dealing with chronic wounds are mainly concerned with closing the wound as quickly as possible to minimize the risk of an infection that could lead to loss of limb or life. Chronic wounds are wounds on patients that have comorbidities that complicate or delay the healing cascade. In one aspect, the grafts described herein can function as a tissue regeneration template that delivers essential wound healing factors, extracellular matrix proteins and inflammatory mediators to help reduce inflammation, enhance healing, and reduce scar tissue formation.

In another aspect, the tissue grafts described herein are useful for addressing or alleviating complications to the spine and surrounding regions that occur after surgery. Acute and chronic spinal injuries and pain can be attributed to trauma and/or degenerative changes in the spinal column. For the degenerative patient, there is usually a progression of possible surgeries depending on the patient's symptoms and disease state. The first surgical option when conservative therapy has failed is a laminectomy or micro-discectomy. These minimally invasive procedures are intended to relieve the pain generator or stenosis of the spinal canal. If there is progression of the disease, then other surgeries may be necessary including, but not limited to, a spinal fusion. Spinal fusions may be achieved through several approaches: anterior (from the front through the abdomen), posterior (from the back), or lateral (through the side). Each approach has advantages and disadvantages. The goal is typically to remove the spinal disc, restore disc height and fuse the two spinal vertebrae together to limit motion and further degradation. There are also surgical options for the surgeon and patient to replace the spinal disc with an artificial disc. Spine trauma is typically treated by fusing the spine levels or if a vertebrae is crushed, the surgeon may choose to do a corpectomy and fusing across the levels that were affected.

In one aspect, the tissue grafts described herein are useful in preventing or reducing scar formation on the spine or near the spine and sealing dural tears. Scar formation at or near the spine after surgery can be very debilitating and possibly require subsequent operations to address the symptoms as discussed above. The term "anti-adhesion" is also used in the art to refer to the prevention of scar tissue at or near the spine. In other aspects, the tissue grafts described herein can be used as a protective barrier, where the graft protects the spinal dura from post-surgical trauma from the surrounding surgical site. For example, the grafts can prevent damage to the spinal dura caused by sharp edges from newly cut bone such as vertebrae. In other aspects, the tissue grafts can be used for anterior lumbar interbody fusion, posterior lumbar interbody fusion trans-lumbar interbody fusion, anterior cervical discectomy and fusion, micro discectomy, spinal dura repair, and as a dura sealant to prevent CSF leakage.

Depending upon the surgical procedure, the tissue graft can be applied directly to the spinal dura, the surrounding region of the spine to include nerve roots, or a combination thereof. Due to the unique structure of vertebrae, the tissue graft can be cut into any shape or dimension so that it can be placed and affixed at the appropriate position in the subject. For example, when the tissue graft is used for bi-lateral coverage, membranes in the shape of a rectangle allow the tissue graft to fit around the posterior spinal process, which minimizes lateral movement. In addition to minimizing lateral movement, the tissue graft can also provide proximal and distal barrier coverage where the spinal lamina has been removed for exposure to the affected area. In one aspect, to ensure proper placement, the graft can be embossed on the exposed basement membrane of the graft to ensure proper placement of the graft in the subject. In particular, proper graft placement will ensure that the basement membrane of the graft is in direct contact with the spinal dura or surrounding region. For example, proper membrane placement and orientation is important when applying the material in spinal applications where a posterior or anterior approach is utilized.

The grafts are useful in preventing or reducing scar formation that can result from a variety of surgical procedures associated with the spine. The grafts can be used after any procedure in the neck, mid-back, or lower back. Depending upon the application, the epithelium of the amnion membrane can be substantially removed. For example, in posterior procedures such as a laminectomy or discectomy, the epithelium layer is substantially removed. Removal of the epithelial cell layer exposes the amnion's basement membrane layer, which increases cell signaling characteristics. This up regulation response enhances cellular migration and expression of anti-inflammatory proteins, which inhibits fibrosis. The spinal dura is typically left unprotected following posterior procedures. Thus, the grafts described herein provide an unmet need in these procedures.

In other aspects, the epithelial cell layer is not removed. For example, in anterior procedures or modified anterior procedures such as Anterior Lumbar Interbody Fusion (ALIF) and Transforaminal Interbody Fusion (TLIF), the amnion epithelium layer is not removed and remains intact. In these aspects, the grafts provide additional protection to the vertebral surgical site by maintaining separation from the peritoneum, larger vessels, and abdominal musculature. The membrane serves as a reduced friction anatomical barrier against adhesions and scaring. For example, the grafts can prevent scar tissue binding major blood vessels to the spine. This is a common problem with post-spinal surgery, which requires a second surgical procedure to address this.

In another aspect, the tissue grafts are useful in dental applications. For example, the grafts can be used around dental implants or in the treatment of advanced gingival recession defect. In another aspect, the grafts can be used in guided tissue regeneration.

In other aspects, the grafts described herein can be used in orthopedic applications (i.e., sports medicine). Sports medicine includes the repair and reconstruction of various soft-tissue injuries in or around joints caused by traumas, or chronic conditions brought about by repeated motion, in active individuals and athletes. For example, sports medicine includes the treatment of a variety of different injuries associated with, but not limited to, shoulders, elbows, feet, ankles hand and wrists.

The main types of injuries include tendon and ligament sprains and ruptures in the various joints, with the most common being ACL in the knee and rotator cuff in the shoulder. Non-tendon and ligament procedures include repair of torn knee meniscus and repair of knee cartilage which if left un-treated can lead to osteoarthritis of the joint. Non-surgical options also include injections of anti-inflammatory drugs to inflamed tendons (such as "tennis elbow"), injection of lubricants into joints (such as hyaluronic acid into the knee), as well as physiotherapy and bracing.

In one aspect, the tissue grafts described herein can be used to wrap tendon repairs to prevent scar formation on the healing tendon. They can also provide a protective, enclosed environment for the repair to progress successfully. The tissue grafts can be used as an off-the-shelf tendon and ligament to replace the need to purchase an allograft or perform tendon or ligament transfer.

In other aspects, the tissue grafts described herein can be used in the reinforcement of rotator cuffs. Some rotator cuff tears are large enough that they require a reinforcement matrix to support the repair due to lack of viable native tissue. The tissue grafts described herein can be used as a matrix to reinforce a repair. In one aspect, the tissue grafts described herein can be used to repair knee cartilage. For example, the tissue grafts can be used as a barrier to hold cell cultured chondrocytes or other pro-cartilage regeneration matrix inside a chondral defect. In this aspect, the tissue graft would be utilized as a flap to close the defect and hold the matrix in place.

In one aspect, the tissue grafts can be used to repair peripheral nerves. The tissue graft can be used as a wrap on nerve repairs to prevent scar formation onto the healing nerve. The tissue graft can also provide a protective enclosed environment for the repair to progress successfully. In other aspects, the tissue grafts can be manufactured into a nerve regeneration tube to guide nerve growth in a protective environment where the nerve ends cannot be re-approximated. Here, nerves can re-attach up to a certain distance if the ends are allowed to meet freely without other soft tissue interfering. In another aspect, the tissue graft can be used to wrap nerve bundles after prostatectomy procedures. These nerves are responsible for erectile function and possible continence. The tissue grafts can be laid on the nerves to keep them from scarring and possibly damaging the nerves.

In other aspects, the tissue grafts described herein can be used in other orthopedic applications such as aid in the repair of periostium; help repair ruptured/damaged bursa; help secure void filling material during bone repair; or in applications involving a subject's extremities (e.g., anti-adhesion barrier for small bone fixation, anti-adhesion barrier where metal plating or hardware is used, or help repair ruptured/damaged bursa).

In another aspect, the tissue grafts can be used in obstetrics and gynecological (OB/GYN) surgical procedures involving the treatment of diseases that may be related to the fertility of the female, pain caused by the reproductive system or cancer in the reproductive system. These procedures include the removal of uterine fibroids (myomectomy), removal of ovarian cysts, tubal ligations, endometriosis treatments, removal of some cancerous or non-cancerous tumors, and vaginal slings. These procedures may be completed through a transvaginal, abdominal or laproscopical approach.

The tissue grafts can be used as a patch to reduce the amount of scar tissue in the reproductive system after a surgical procedure. Scar tissue is another form of fibrous tissue and may also contribute to fertility problems. The ability to minimize the amount of scar on the ovaries, or within the fallopian tubes may help with post-operative fertility and even pain. In another aspect, the tissue grafts can be used to reline the uterine wall after severe endometriosis treatments and increase the patient's ability to conceive. In a further aspect, the tissue graft can be used as an anti-adhesion barrier after removal of ovarian cyst or aid in the repair of vaginal wall erosion.

In other aspects, the tissue grafts can be used in cardiac applications. Angina is severe chest pain due to ischemia (a lack of blood, thus a lack of oxygen supply) of the heart muscle, generally due to obstruction or spasm of the coronary arteries (the heart's blood vessels). Coronary artery disease, the main cause of angina, is due to atherosclerosis of the cardiac arteries. Various open cardiac and vascular surgery procedures to remove atherosclerotic clots require the repair, reconstruction and closure of the vessel, and the support of a regenerative tissue patch to close and patch the surgical defect. Heart by-pass grafts and heart defect reconstruction (as part of an open-heart surgical procedure) also can benefit from a patch or graft to provide a buttress to soft-tissue weakness, tissue replacement if there is a lack of suitable tissue, and also the potential to reduce adhesions to the heart itself. The tissue grafts described herein can be used as a patch to support the repair of vascular and cardiac defects caused by operations and complications such as carotid artery repair, coronary artery bypass grafting, congenital heart disease, heart valve repair, and vascular repair (i.e. peripheral vessels).

The tissue grafts described herein can be used in general surgery procedures. For example, general surgical procedures include procedures related to the abdominal cavity. These include the intestines, stomach, colon, liver, gallbladder, appendix, bile ducts and thyroid glands. Procedures may include hernias, polypectomy, cancer removal, surgical treatment of Crohn's and ulcerative colitis. These procedures may be done open or laparoscopically. In other aspects, the tissue grafts can be used to facilitate closure of anastomosis, an anti-adhesion barrier for anastomosis, or an anti-adhesion barrier for hernia repair.

In other aspects, the tissue grafts can be used in ENT procedures. Tympanoplasty is performed for the reconstruction of the eardrum (tympanic membrane) and/or the small bones of the middle ear. There are several options for treating a perforated eardrum. If the perforation is from recent trauma, many ear, nose and throat specialists will elect to watch and see if it heals on its own. If this does not occur or frequent re-perforation occurs in the same area, surgery may be considered. Tympanoplasty can be performed through the ear canal or through an incision behind the ear. Here, the surgeon harvests a graft from the tissues under the skin around the ear and uses it to reconstruct the eardrum. The tissue grafts described herein can be used to prevent the additional trauma associated with harvesting the patients' own tissue and save time in surgery. In other aspects, the tissue grafts can be used as a wound covering after adenoidectomy, a wound cover after tonsillectomy, or facilitate repair of the Sniderian membrane.

In other aspects, the tissue grafts described herein can be used in plastic surgery procedures. Scar revision is surgery to improve or reduce the appearance of scars. It also restores function and corrects skin changes (disfigurement) caused by an injury, wound, or previous surgery. Scar tissue forms as skin heals after an injury or surgery. The amount of scarring may be determined by the wound size, depth, and location; the person's age; heredity; and skin characteristics including skin color (pigmentation). Surgery involves excision of the scar and careful closure of the defect. In one aspect, the tissue grafts described herein can be used as a patch to aid in the healing and prevention of scars; and keloid or cancer revision/removal where careful approximation of soft-tissue edges is not achievable and scar tissue can result. Additionally, the anti-inflammatory properties of the tissue graft can enhance healing as well.

In other aspects, the tissue grafts can be used in opthalmological applications (e.g., on-lay grafts ocular surface repair) or urological applications (e.g., facilitate closure of the vas deferens during vasectomy reversal or facilitate closure of the vas deferens resulting from trauma).

Depending upon the application of the graft, the graft can be soaked with a bioactive agent such as a solution composed of naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Here, one or more membrane layers of the tissue graft absorb the bioactive agent. Upon application of the wet tissue graft with bioactive agent to the wound, the bioactive agent is delivered to the wound over time.

Although the tissue grafts described herein can be applied directly to the tissue of a subject, they can also be applied to a wound dressing that can subsequently be applied to the subject. For example, the wound dressing can be gauze, a bandage or wrap, or any other suitable article capable of containing or affixing the tissue graft that can be applied directly to a subject.

Various modifications and variations can be made to the articles, compositions and methods described herein. Other aspects of the articles, compositions and methods described herein will be apparent from consideration of the specification and practice of the articles, compositions and methods disclosed herein. It is intended that the specification and examples be considered as exemplary.

What is claimed:

1. A method for enhancing wound healing in a subject comprising applying to the wound a placental tissue graft produced by the method comprising:
   a) laminating at least two placental tissues together;
   b) chemically dehydrating the placental tissues; and
   c) freeze-drying the placental tissues to produce the tissue graft,
   wherein the at least two placental tissues are selected from the group consisting of: (1) at least two layers of chorion, (2) at least two layers of cellularized amnion membrane, and (3) at least one layer of chorion and at least one layer of cellularized amnion membrane.

2. The method of claim 1, wherein the wound is a chronic wound.

3. The method of claim 1, wherein the wound is an acute wound.

4. A method for preventing or reducing scar formation on or near the spine of a subject after a surgical procedure, the method comprising applying directly to the spinal dura of the subject or a region near the spine a placental tissue graft produced by the method comprising:
   a) laminating at least two placental tissues together;
   b) chemically dehydrating the placental tissues; and
   c) freeze-drying the placental tissues to produce the tissue graft,
   wherein the at least two placental tissues are selected from the group consisting of: (1) at least two layers of chorion, (2) at least two layers of cellularized amnion membrane, and (3) at least one layer of chorion and at least one layer of cellularized amnion.

5. The method of claim 4, wherein the surgical procedure comprises a posterior approach spinal procedure.

6. The method of claim 5, wherein the posterior approach spinal procedure is a laminectomy or discectomy.

7. The method of claim 5, wherein the posterior approach spinal procedure is an Anterior Lumbar Interbody Fusion (ALIF) or Transforaminal Lumbar Interbody Fusion (TLIF).

8. The method of claim 4, wherein the surgical procedure comprises an anterior approach spinal procedure.

9. The method of claim 4, wherein the surgical procedure comprises a lateral approach spinal procedure.

10. A method for regenerating and/or repairing tissue in a subject, the method comprising applying to the tissue in need of regeneration and/or repair a placental tissue graft produced by the method comprising:
    a) laminating at least two placental tissues together;
    b) chemically dehydrating the placental tissues; and
    c) freeze-drying the placental tissues to produce the tissue graft,
    wherein the at least two placental tissues are selected from the group consisting of: (1) at least two layers of chorion, (2) at least two layers of cellularized amnion membrane, and (3) at least one layer of chorion and at least one layer of cellularized amnion; and
    wherein the method for regenerating and/or repairing a tissue is selected from the group consisting of repairing a dural tear, eliminating a frenum pull, regenerating lost patella tissue, repairing damaged Schneiderian membrane in the sinus cavity, regenerating soft tissue around dental implants, performing a vestibuloplasty, repairing periosteum, repairing ruptured or damaged bursa, reinforcing rotator cuffs, performing a tympanoplasty, repairing ocular surfaces, facilitating closure of the vas deferens facilitating closure of anastomosis, patching vasculature and/or cardiac defects, and promoting wound healing after plastic surgery.

11. The method of claim 10, wherein the placental tissue graft is applied directly to spinal dura, a surrounding region of a spine including nerve roots, or a combination thereof.

12. The method of claim 10, wherein the placental tissue graft is applied directly to a bone.

13. The method of claim 12, wherein the bone is a vertebra.

* * * * *